(12) United States Patent
Kheiri et al.

(10) Patent No.: US 9,176,109 B2
(45) Date of Patent: Nov. 3, 2015

(54) CARTRIDGE AND SENSOR-DISPENSING INSTRUMENT

(71) Applicant: Bayer HealthCare LLC, Whippany, NJ (US)

(72) Inventors: Mohammad A. Kheiri, Plainfield, IN (US); D. Glenn Purcell, Edwardsburg, IN (US)

(73) Assignee: Bayer HealthCare LLC, Whippany, NJ (US)

(*) Notice: Subject to any disclaimer, the term of this patent is extended or adjusted under 35 U.S.C. 154(b) by 0 days.

(21) Appl. No.: 14/267,986

(22) Filed: May 2, 2014

(65) Prior Publication Data

US 2014/0241958 A1 Aug. 28, 2014

Related U.S. Application Data

(63) Continuation of application No. 14/083,287, filed on Nov. 18, 2013, now Pat. No. 8,758,700, which is a continuation of application No. 13/415,695, filed on Mar. 8, 2012, now Pat. No. 8,609,037, which is a (Continued)

(51) Int. Cl.
*G01N 33/48* (2006.01)
*G01N 33/487* (2006.01)
*B01L 3/00* (2006.01)

(52) U.S. Cl.
CPC .............. *G01N 33/48* (2013.01); *B01L 3/523* (2013.01); *B01L 3/527* (2013.01); *G01N 33/48757* (2013.01); *Y10T 436/193333* (2015.01)

(58) Field of Classification Search
CPC .............. G01N 33/48757; G01N 2035/00089; B01L 3/505; B01L 2200/027; B01L 2300/0825; B01L 3/523; B01L 99/00
See application file for complete search history.

(56) References Cited

U.S. PATENT DOCUMENTS

| | | | |
|---|---|---|---|
| 5,759,010 A | 6/1998 | Jacobs et al. | 414/796.8 |
| 6,378,702 B1 | 4/2002 | Kintzig | 206/456 |

(Continued)

FOREIGN PATENT DOCUMENTS

| | | |
|---|---|---|
| EP | 1 347 296 A2 | 9/2003 |
| JP | 60 055263 | 3/1985 |

(Continued)

OTHER PUBLICATIONS

Written Opinion corresponding to International Patent Application Serial No. PCT/US2005/022843 dated Oct. 5, 2005, 6 pages.

(Continued)

*Primary Examiner* — Sally Merkling
(74) *Attorney, Agent, or Firm* — Nixon Peabody LLP

(57) ABSTRACT

A disposable cartridge adapted to be used with a sensor-dispensing instrument comprises a housing, test sensors, a mechanical mechanism and moveable seals. The housing forms at least one opening therethrough. The test sensors are stacked in the housing. The test sensors are adapted to assist in testing at least one analyte. The mechanical mechanism is adapted to urge the test sensors in a first direction. One of the test sensors is positioned for ejection from the cartridge. The moveable seals is adapted to be in a closed position that seals the at least one opening so as to provide a substantially moisture-proof and a substantially air-tight cartridge, and one of the moveable seals is adapted to be in an open position that allows one of the test sensors to be moved therethrough.

17 Claims, 18 Drawing Sheets

Related U.S. Application Data continuation of application No. 11/630,124, filed as application No. PCT/US2005/022843 on Jun. 23, 2005, now Pat. No. 8,153,080.

(60) Provisional application No. 60/582,712, filed on Jun. 24, 2004, provisional application No. 60/617,825, filed on Oct. 12, 2004.

(56) References Cited

U.S. PATENT DOCUMENTS

| | | | |
|---|---|---|---|
| 6,908,008 B2 | 6/2005 | Pugh | 221/135 |
| 6,997,343 B2 | 2/2006 | May et al. | 221/232 |
| 7,582,262 B2 | 9/2009 | Funke et al. | 422/430 |
| 2002/0104849 A1 | 8/2002 | Giruad | 221/270 |
| 2003/0089730 A1 | 5/2003 | May et al. | 221/232 |
| 2004/0178216 A1* | 9/2004 | Brickwood et al. | 221/268 |
| 2008/0131322 A1 | 6/2008 | Kheiri et al. | 422/82.01 |

FOREIGN PATENT DOCUMENTS

| | | |
|---|---|---|
| JP | 60 055264 | 3/1985 |
| RU | 2219585 | 12/2003 |

OTHER PUBLICATIONS

International Search Report corresponding to International Patent Application Serial No. PCT/US2005/022843, dated Oct. 5, 2005, 4 pages.

* cited by examiner

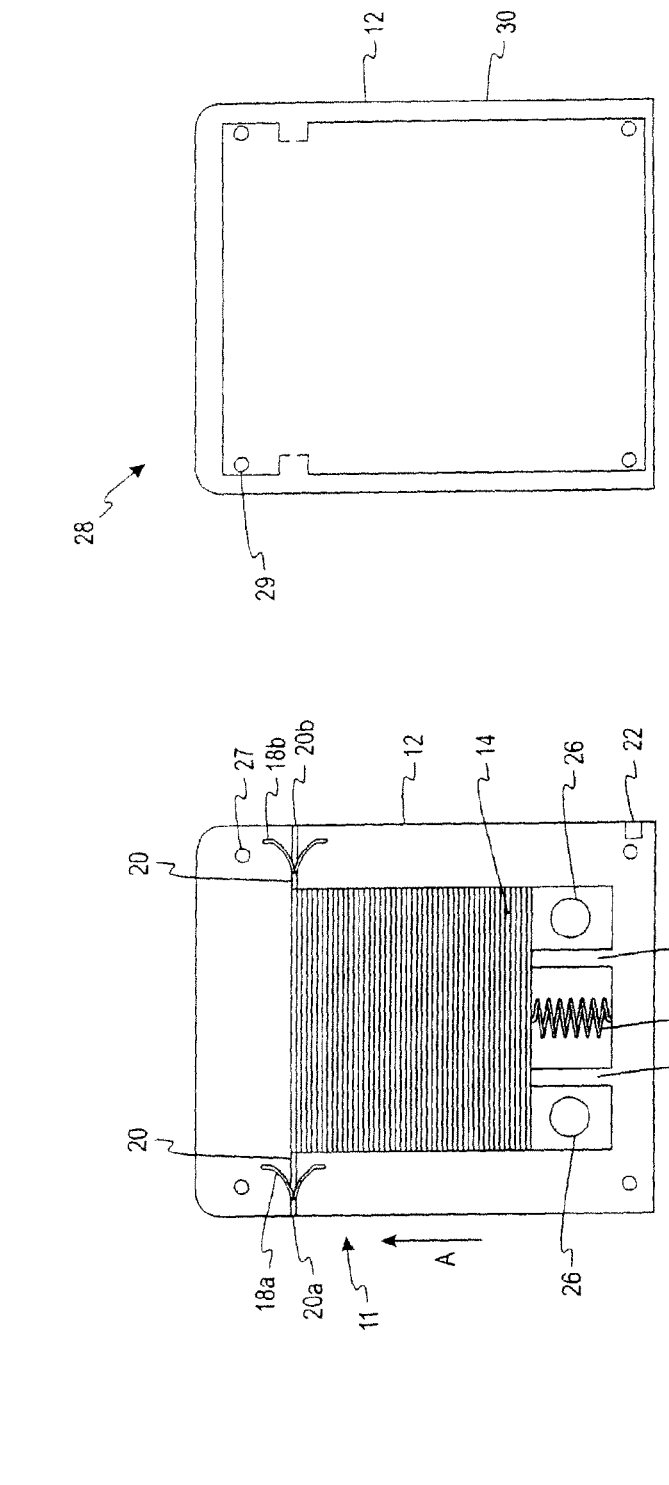

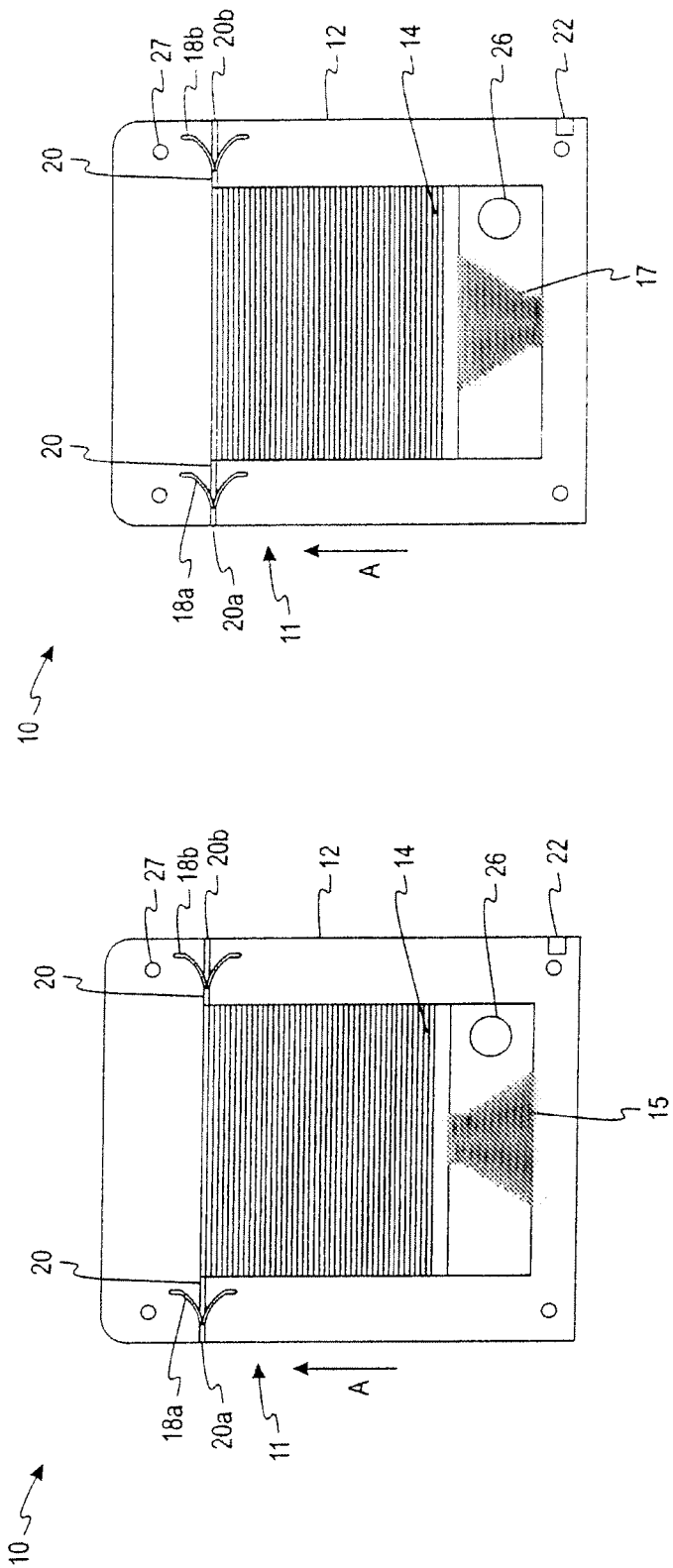

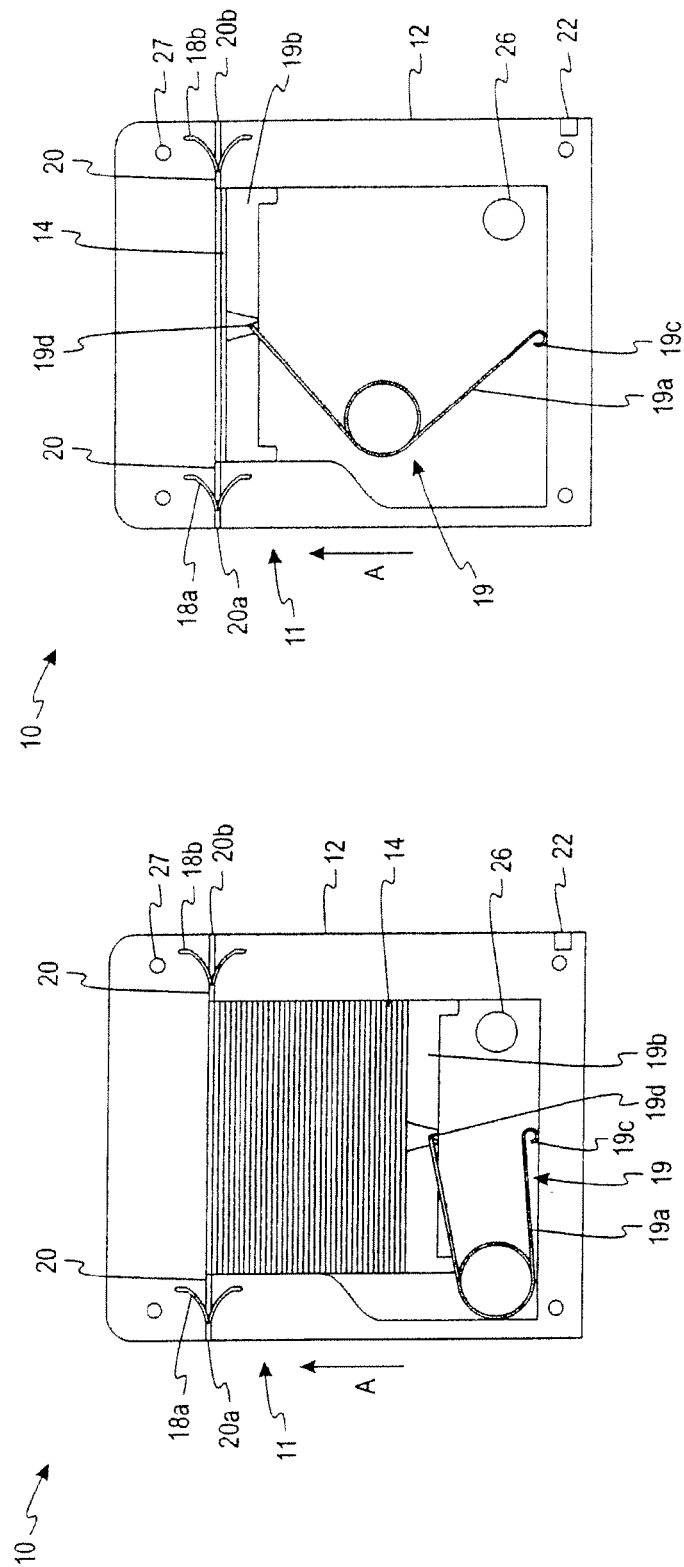

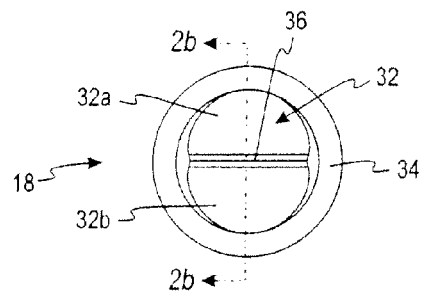
*Fig. 2a*
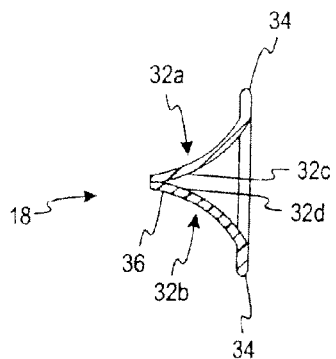   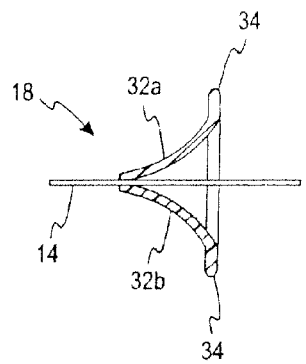
*Fig. 2b*     *Fig. 2c*
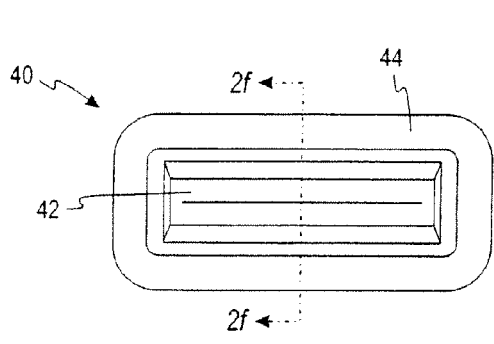   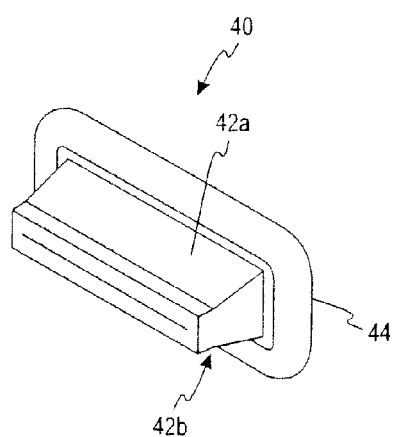
*Fig. 2d*     *Fig. 2e*

CARTRIDGE AND SENSOR-DISPENSING INSTRUMENT

CROSS-REFERENCE TO RELATED APPLICATIONS

This application is a continuation of prior application Ser. No. 14/083,287, filed Nov. 18, 2013, now allowed, which is a continuation of prior application Ser. No. 13/415,695, filed Mar. 8, 2012, now issued as U.S. Pat. No. 8,609,037, which is a continuation of prior application Ser. No. 11/630,124, filed Dec. 19, 2006, now issued as U.S. Pat. No. 8,153,080, which was the National Stage of International Application No. PCT/US2005/022843, filed Jun. 23, 2005, which claims the benefit of U.S. Provisional Application No. 60/582,712, filed Jun. 24, 2004, and U.S. Provisional Application No. 60/617,825, filed Oct. 12, 2004, each of which is hereby incorporated by reference herein in its entirety.

FIELD OF THE INVENTION

The present invention generally relates to a cartridge and sensor-dispensing instrument, and, more particularly, to a cartridge that multiple sensors that are used in analyzing blood glucose or other analytes contained therein.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. While the remainder of the disclosure herein will be directed towards determining glucose, it is to be understood that the methods of this invention may be used for determining other analytes on selection of an appropriate enzyme.

The results of such tests can be used to determine what, if any, insulin or other medication needs to be administered. In one type of blood glucose testing system, sensors are used to test a fluid such as a sample of blood.

A sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested is supplied to contact areas located near the rear or contact end of the sensor.

Such a sensor is often sensitive to the effects of ambient humidity. One way to reduce or eliminate the effects of ambient humidity is to individually package each of the sensors with desiccant. Such a method has a drawback of requiring the unpacking of a strip before each use. Thus, it would be desirable to have a cartridge that would contain a plurality of test sensors that would not require unpacking each strip before using. Also, for the convenience and case of use, it would also be desirable to have a simple mechanism to feed the test sensors one at a time for testing by the user. This provides ease of use to normal users and is especially important for those users who may have some physical limitations.

SUMMARY OF THE INVENTION

According to one embodiment, a disposable cartridge is adapted to be used with a sensor-dispensing instrument. The disposable cartridge comprises housing, a plurality of test sensors, a mechanical mechanism, and a plurality of moveable seals. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for ejection from the cartridge. The plurality of moveable seals is adapted to be in a closed position that seals the at least one opening so as to provide a substantially moisture-proof and a substantially air-tight cartridge. One of the plurality of moveable seals is adapted to be in an open position that allows one of the plurality of test sensors to be moved therethrough.

According to another embodiment, a disposable cartridge is adapted to be used with a sensor-dispensing instrument. The disposable cartridge comprises housing, a plurality of test sensors, a mechanical mechanism, and at least one moveable seal. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. The moveable seal is adapted to be in a closed position that seals the at least one opening so as to provide a substantially moisture-proof and a substantially air-tight cartridge. The moveable seal is adapted to be in an open position that allows one of the plurality of test sensors to be moved therethrough.

According to one embodiment, a sensor-dispensing instrument comprises a disposable cartridge, instrument housing, and a pusher assembly. The disposable cartridge comprises housing, a plurality of test sensors, a mechanical mechanism, and at least one moveable seal. The housing forms at least one opening therethrough. The plurality of test sensors is stacked in the housing. The plurality of test sensors is adapted to assist in testing at least one analyte. The mechanical mechanism is adapted to urge one of the plurality of test sensors in a first direction. One of the plurality of test sensors is positioned for ejection from the cartridge. The at least one moveable seal is adapted to be in a closed position that seals the at least one opening so as to provide a substantially moisture-proof and a substantially air-tight cartridge. The at least one moveable seal is adapted to be in an open position that allows one of the plurality of test sensors to be moved therethrough. The housing forms a dispensing outlet and is adapted to receive the disposable cartridge. The pusher assembly includes a slider and a thin flat bar coupled to the pusher assembly. The flat bar is adapted to slide from a first position to a second position on movement of the pusher assembly. During the movement of the flat bar from the first position to the second position, the flat bar contacts one of the plurality of test sensors and pushes it at least partially through at least one of the moveable seals.

According to a further embodiment, a disposable cartridge is adapted to be used with a sensor-dispensing instrument. The disposable cartridge comprises a housing, a plurality of test sensors, a mechanical mechanism comprising a torsion spring, and a plurality of moveable seals. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for ejection from the cartridge. The plurality of moveable seals is adapted to be in a closed position that seals the at least one opening so as to provide a substantially moisture-proof and a substantially air-tight cartridge. One of the plurality of moveable seals is adapted to be in an open position that allows one of the plurality of test sensors to be moved therethrough.

According to yet another embodiment, a disposable cartridge is adapted to be used with a sensor-dispensing instrument. The disposable cartridge comprises a housing, a plurality of test sensors, a mechanical mechanism comprising a torsion spring, and at least one moveable seal. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. The moveable seal is adapted to be in a closed position that seals the at least one opening so as to provide a substantially moisture-proof and a substantially air-tight cartridge. The moveable seal is adapted to be in an open position that allows one of the plurality of test sensors to be moved therethrough.

According to another embodiment, a sensor-dispensing instrument comprises a disposable cartridge, instrument housing, and a mechanism for separating a single sensor from a stack of a plurality of sensors. The disposable cartridge comprises a housing, a plurality of test sensors, a mechanical mechanism comprising a torsion spring, and at least one moveable seal. The housing forms at least one opening therethrough. The plurality of test sensors is stacked in the housing. The plurality of test sensors is adapted to assist in testing at least one analyte. The mechanical mechanism is adapted to urge one of the plurality of test sensors in a first direction. One of the plurality of test sensors is positioned for ejection from the cartridge. The at least one moveable seal is adapted to be in a closed position that seals the at least one opening so as to provide a substantially moisture-proof and a substantially air-tight cartridge. The at least one moveable seal is adapted to be in an open position that allows one of the plurality of test sensors to be moved therethrough. The housing forms a dispensing outlet and is adapted to receive the disposable cartridge. The mechanism for separating a single sensor from a stack of a plurality of sensors involves a pusher assembly. The pusher assembly includes a slider and a thin flat bar coupled to the pusher assembly. The flat bar is adapted to slide from a first position to a second position on movement of the pusher assembly. During the movement of the flat bar from the first position to the second position, the flat bar contacts one of the plurality of test sensors and pushes it at least partially through at least one of the moveable seals.

BRIEF DESCRIPTION OF THE DRAWINGS

FIG. 1a is a front view of a main-housing portion of a cartridge according to one embodiment of the present invention.

FIG. 1b is a front view of a lid-housing portion of a cartridge according to one embodiment of the present invention.

FIG. 1d is the front view of the main-housing portion of the cartridge of FIG. 1a with a conical spring.

FIG. 1e is the front view of the main-housing portion of the cartridge of FIG. 1a with an inverted conical spring.

FIG. 1f is the front view of the main-housing portion of a modified cartridge of FIG. 1a with a torsion spring in a closed position.

FIG. 1g is the front view of the main-housing portion of the modified cartridge of FIG. 1a with a torsion spring in an open position.

FIG. 2a is a top view of a duckbill seal according to one embodiment.

FIG. 2b is a cross-sectional view taken generally along line 2b-2b of FIG. 2a.

FIG. 2c is the cross-sectional view of FIG. 2b in an open position with a test sensor.

FIG. 2d is a top view of a duckbill seal according to another embodiment.

FIG. 2e is a perspective view of the seal of FIG. 2d.

FIG. 7b is a side view of the cartridge of FIG. 7a.

FIG. 8b is a side view of the cartridge of FIG. 8a.

Figure 1C:
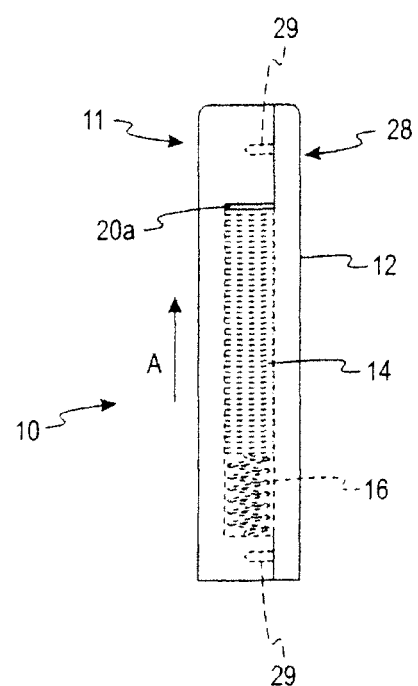
FIG. 1c is a side view of the cartridge of FIGS. 1a and 1b.
Figure 2F:
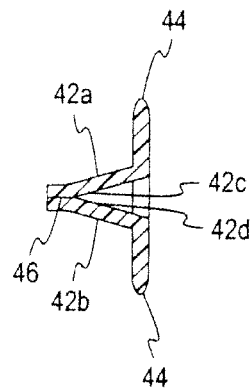
FIG. 2f is a cross-sectional view taken generally along line 2f-2f of FIG. 2d.
Figure 2G:
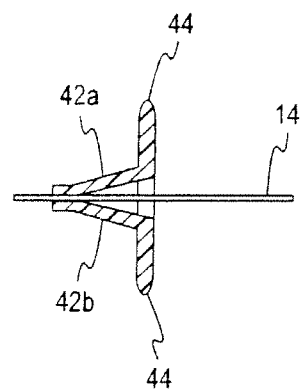
FIG. 2g is the cross-sectional view of FIG. 2f in an open position with a test sensor.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE ILLUSTRATED EMBODIMENTS

The present invention is directed to a disposable cartridge that contains a plurality of test sensors. The plurality of test sensors is used to determine concentrations of analytes. Analytes that may be measured using the present invention include glucose, lipid profiles (e.g., cholesterol, triglycerides, LDL and HDL), microalbumin, hemoglobin $A_1C$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

Disposable Cartridges

Referring to the drawings, a disposable cartridge 10 in FIGS. 1a-1c is shown that is adapted to be used in a sensor-dispensing instrument. The cartridge 10 is a substantially moisture-proof and air-tight device. The disposable cartridge 10 of FIGS. 1a,c comprises a housing 12, a plurality of test sensors 14, a mechanical mechanism 16, and a plurality of moveable seals 18. The housing 12 for the disposable cartridge 10 may contain a first section (main-housing section 11 in FIG. 1a) and a second section (lid-housing section 28 in FIG. 1b) that are joined together. The cartridge 10 is adapted to be disposable after each of the plurality of test sensors 14 has been used. After each of the plurality of test sensors 14 has been used, the cartridge 10 may be removed from the sensor-dispensing instrument and replaced with a second identical cartridge that includes a plurality of unused test sensors.

Referring to FIG. 1a, the housing 12 forms at least one opening 20 therethrough. The opening 20 is sealed at two locations using the plurality of moveable seals 18a,b. The moveable seals 18a,b prevent or inhibit air and moisture from entering into the interior of the cartridge 10 that contains the plurality of test sensors 14. The opening 20 is sized to allow the plurality of test sensors 14 to move therethrough one at a time and eventually exit the cartridge 10. Specifically, the plurality of test sensors 14, one at a time, exits the cartridge 10 via an opening end 20a. As will be discussed below in more detail, the housing 12 may also form at least one notch 22 to assist in holding the cartridge in position within the sensor-dispensing instrument.

The housing 12 may be made of a variety of materials, but is typically made of polymeric material. Some examples of polymeric materials that may be used in forming the housing 12 include polycarbonate, ABS, nylon, polystyrene, polypropylene, or combinations thereof. Other additives may be added in forming the housing such as, for example, TEFLON® for lubrication or glass to provide strength. It is contemplated that other additives may be employed. Polycarbonate is desirable for several reasons including being a durable material and having an ability to prevent or inhibit air (especially oxygen and moisture) from entering the housing 12. Additionally, if the housing is formed from two distinct sections, polycarbonate is capable of sealing to itself. This may be desirable in a process where the two housing sections are sonically welded.

In one example, the housing 12 includes the main-housing section 11 and the lid-housing section 28. The lid-housing section 11 of FIG. 1b has a plurality of guide pins 29 for precisely locating the lid-housing section 28 with respect to the main-housing section 11. The main-housing section 11 of FIG. 1a forms a plurality of apertures 27 for receiving a respective one of the guide pins 29 of the lid-housing section 11 before being joined together by, for example, sonic welding. To assist in reducing or eliminating moisture and air from entering the housing, at least one energy director 30 may be added to the lid-housing section 28 (such as shown in FIG. 1b) that assist in sealing the perimeter of the housing. Alternatively, the at least one energy director may be added to the main-housing section. The energy directors 30 melt and form a seal around the perimeter of the housing 12. Alternatively, it is contemplated that guide pins may be located on the main-housing section and the lid-housing section forms apertures for receiving such guide pins. The energy directors 30 are desirably located to maximize the sealing of the housing 12.

The housing 12 may be formed by processes known to those skilled in the art including injection-molding processes. If injection-molding processes are used, the wall thicknesses are typically designed within normal ranges. It is contemplated that other processes may be used such as a molding process.

As shown in FIGS. 1a,c, the plurality of test sensors 14 is stacked in the housing 12. The plurality of test sensors 14 is adapted to assist in testing at least one analyte. As discussed above, one of the analytes that may be tested is glucose from, for example, a whole blood sample. In one embodiment, the plurality of test sensors would include an appropriately selected enzyme to react with the desired analyte or analytes to be tested. An enzyme that may be used to react with glucose is glucose oxidase. It is contemplated that other enzymes may be used such as glucose dehydrogenase. An example of a test sensor 14 is disclosed in U.S. Pat. No. 6,531,040 assigned to Bayer Corporation. It is contemplated that other test sensors may be used in the disposable cartridge 10.

The plurality of test sensors 14 may vary in number than shown in FIGS. 1a, 1c so as to address the needs of different users. Typically, the stacked test sensors contain from about 10 to about 50 or 100 sensors and, more specifically, contain from about 25 to about 40 sensors. Because of limited shelf- and use-life of the test sensors, it is envisioned that a user who tests infrequently would likely desire a cartridge having less test sensors as opposed to a user who tests more frequently.

To urge the stacked test sensors 14 upwardly (in the direction of arrow A in FIGS. 1a,c), the mechanical mechanism 16 is used according to one embodiment. The mechanical mechanism 16 assists in positioning one of the plurality of test sensors for eventual ejection from the cartridge 10 via opening end 20a. The mechanical mechanism is any device that can urge pressure on the stacked test sensors 14 so as to position one of the plurality of test sensors for ejection. For example, the mechanical mechanism 16 depicted in FIGS. 1a,c is a spring. Various types of springs may be used as the mechanical mechanism to urge the stacked test sensors 14 in the direction of arrow A in FIGS. 1a,c. For example, the spring may be a compression spring or a torsion spring. Springs are desirable because of their simplicity and ease of use.

Another specific type of compression spring is shown in FIGS. 1d, 1e. The cartridge 10 of FIG. 1d is the same as FIG. 1a except that the mechanical mechanism 15 is a conical spring. The cartridge 10 of FIG. 1e is also the same as FIG. 1a except that the mechanical mechanism 17 is a conical spring. The conical spring 17 of FIG. 1e is inverted as compared to the conical spring 15 of FIG. 1d.

According to an embodiment of the invention shown in FIGS. 1f, 1g, a modified cartridge 12 includes a mechanical mechanism 19 that comprises a torsion spring 19a and a movable pressure plate 19b. The movable pressure plate 19b contacts the stack of test sensors. The torsion spring 19a includes a fixed end member 19c that attaches the torsion spring 19a to the cartridge housing 12. The torsion spring 19a also includes a movable end member 19*d* that is attached to a pivot point on the pressure plate 19*b*. The torsion spring 19*a* is located to the side of the stack of test sensors 14. The torsion spring 19*a* exerts pressure on the stack of test sensors 14 and facilitates the upward movement of the test sensors in the direction of the arrow A in FIGS. 1*f* and 1*g*. At the same time, the pressure plate 19*b* moves in the same direction and holds the remainder of the sensor stack 14 in place.

Additionally, the mechanical mechanism 16 may be a ratchet pusher. Using such an embodiment, the ratchet pusher automatically ratchets the stacked test sensors upwardly (i.e., the direction of arrow A in FIGS. 1 *a, c*). The ratchet pusher would desirably need to extend the length of the interior of the cartridge such that all of test sensors would eventually be used. It is contemplated that the ratchet pusher may be used in combination with one or more springs.

To assist in guiding the mechanical mechanism 16 upwardly (in the direction of arrow A in FIGS. 1 *a,c*), the housing 12 has been formed with a plurality of prongs or extensions 24. The optional prongs or extensions 24 assist in guiding the mechanical mechanism 16 in a generally upwardly direction, thus making movement of the plurality of test sensors in the direction of arrow A easier.

To assist in protecting the reagent(s) in the test sensors 14, desirable packaging material and/or desiccant material may be used. The disposable cartridge 10 is typically packaged in material that prevents or inhibits air from entering into an interior of the housing 12 that contains the test sensors 14. One type of removable packaging that may be used to enclose the disposable cartridge 10 is aluminum foil. It is contemplated that other types of removable packaging may be employed. It is contemplated that desiccant material may be added in the interior of the removable packaging to assist in maintaining an appropriate humidity level therein. If the reagent in the test sensors is not humidity sensitive, then there is little or no need to include much, if any, desiccant. The removable packaging with or without the desiccant material assists in increasing the shelf-use of the test sensors. The removable packaging is to be removed before the cartridge 10 is placed into the sensor-dispensing instrument.

It is contemplated that the disposable cartridge 10 may be initially placed in a polymeric container such as a bottle or other type of container. The container may be shaped similarly to the disposable cartridge with a desirable seal to prevent or inhibit air or moisture from entering the interior of the container. The container may include a lid that is attached to the remainder of the container via a living hinge. It is contemplated that desiccant may also be added within the container. The container with or without the desiccant material assists in increasing the shelf-use of the test sensors. The disposable cartridge 10 is removed from the container before being placed into the sensor-dispensing instrument.

Desiccant material 26 is desirably added to the disposable cartridge 10 to assist in maintaining an appropriate humidity level within the interior of the housing 12 that contains the test sensors 14. Specifically, some moisture may enter the interior of the housing 12 whenever a sensor is pushed out from the disposable cartridge, but such moisture is desirably absorbed by the desiccant so as to protect the reagent in the test sensors from degradation. By maintaining an appropriate humidity level, reagent material in the test sensors is protected. The amount of desiccant material 26 should be sufficient to obtain the desired shelf-life (the time period before any of the plurality of test sensors are used). More specifically, the shelf-life typically refers to the time period before the cartridge 10 is removed from the packaging material, if used. The amount of desiccant material 26 should also be sufficient to obtain the desired use-life (the time period after first use of one of the plurality of test sensors). More specifically, the use-life typically refers to the time period after the cartridge 10 is removed from the packaging material, if used.

Examples of desiccant that may be included within the disposable container, the removable packaging enclosing the disposable container, or the container containing the disposable cartridge include commercially available desiccants. The desiccant may be in the form of several shapes including balls, tablets, granular, or paper. For example, the desiccant may be molecular sieve spheres or thick desiccant paper. The desiccant may be placed within the interior of the housing 12 such as shown with desiccant material 26. The desiccant may be molded into an interior surface of the housing 12 of the cartridge so as to absorb moisture within the same. One non-limiting example of desiccant material may be purchased from Multisorb of Buffalo, N.Y. in the form of, for example, molecular sieve beads.

It is contemplated that desiccant may not be used for test sensors that are not humidity sensitive. The amount of desiccant used, if any, depends on how humidity sensitive the test sensor is and the duration of the desired use-life.

The seals 18*a,b* are adapted to move from closed positions (shown in FIG. 1*a*) to open positions. In a closed position, the plurality of seals 18*a,b* seals the interior of the housing 12 containing the test sensors 14. In such a closed position, the plurality of seals 18*a,b* provides a substantially moisture-proof and a substantially air-tight cartridge. The plurality of seals 18*a,b* is desirably designed to prevent or inhibit moisture from entering via either opening ends 20*a,b* and effecting the plurality of test sensors 14 for at least the shelf-life and use-life of the plurality of sensors. When the moveable seal 18*a* is in an open position, the test sensors 14, one at a time, can be moved through the opening 20 so as to eventually exit via the opening end 20*a*.

One type of moveable seal that may be used in the cartridge 10 is a duckbill seal. The moveable seals 18*a,b* of FIG. 1*a* are duckbill seals. Referring to FIGS. 2*a*-2*g*, two duckbill seals 18, 40 are shown that may be used as moveable seals in the cartridge.

Referring to FIGS. 2*a*-2*c*, the duckbill seal 18 is shown with a generally pyramidal section 32 located in the middle thereof and a circumferentially-extending circular section 34. The generally pyramidal section 32 includes a first outwardly-extending portion 32*a* and a second outwardly-extending portion 32*b*. The first outwardly-extending portion 32*a* includes a surface 32*c* and the second outwardly-extending portion 32*b* includes a surface 32*d*. In a closed position (FIGS. 2*a,b*), a portion 36 of each of the surfaces 32*c,d* abuts each other to form a substantially moisture-proof and substantially air-tight seal. In an open position (FIG. 2*c*), the first outwardly-extending portion 32*a* and the second outwardly-extending portion 32*b* are moved or urged away from each other so as to allow a test sensor 14 to proceed therethrough.

Referring next to FIGS. 2*d*-2*g*, the duckbill seal 40 is shown with a generally truncated rectangular section 42 located in the middle thereof and a circumferentially-extending rectangular section 44. The generally rectangular section 42 includes a first outwardly-extending portion 42*a* and a second outwardly-extending portion 42*b*. The first outwardly-extending portion 42*a* includes a surface 42*c* and the second outwardly-extending portion 42*b* includes a surface 42*d*. In a closed position (FIGS. 2*d-f*), a portion 46 of each of the surfaces 42*c,d* abuts each other to form a substantially moisture-proof and substantially air-tight seal. In an open position (FIG. 2*g*), the first outwardly-extending portion 42*a* and the second outwardly-extending portion 42*b* are moved or urged away from each other so as to allow a test sensor 14 to proceed therethrough. It is contemplated that the duckbill seals may be shaped differently than depicted in FIGS. 2a-2g with duckbill seals 18, 40.

The duckbill seals 18, 40 of FIGS. 2a-2g may be made of materials such as polymeric materials. For example, silicon (e.g., medical-grade silicon), rubber, plastomers, elastomers, or other flexible polymeric materials may be used in forming the duckbill seals. The duckbill seals 18, 40 need a certain degree of memory. Memory as that term is used herein is the ability of a material to return to substantially the same position after being moved or stretched.

Figure 3A:
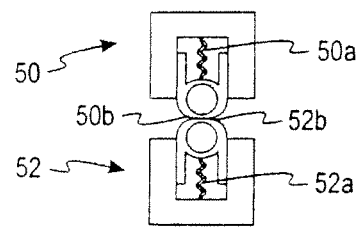
FIG. 3a is a top view of a seal according to a further embodiment.
Figure 3B:
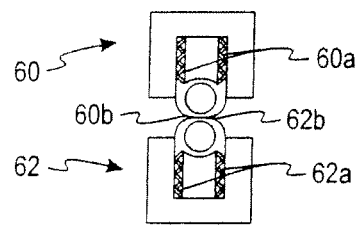
FIG. 3b is a top view of a seal according to one embodiment.

It is contemplated that other type of moveable seals may be used in the disposable cartridge. For example, spring seals are shown in FIGS. 3a, 3b. For cost-efficiency and ease of manufacturer, it is desirable for the spring seals to be made from extruded polymers. It is contemplated, however, that the spring seals may be formed by a molding process.

Referring to FIG. 3a, a spring seal 50 includes a spring section 50a and a sealing surface 50b. Similarly, a spring seal 52 includes a spring section 52a and a sealing surface 52b. The seals 50, 52 function together to form a closed position as shown in FIG. 3a. More specifically, the sealing surfaces 50a, 52b abut each other. The seals 50, 52 may be made of material such as silicon (e.g., medical-grade silicon), rubber, plastomers, elastomers, or other flexible polymeric materials. The seals 50, 52 need a certain degree of memory. It is contemplated that the spring sections of the seals 50, 52 may also be made of material such as metal.

Another type of spring seal is shown in FIG. 3b with spring seals 60, 62. The spring seal 60 includes two spring sections 60a and a sealing surface 60b. Similarly, a spring seal 62 includes two spring sections 62a and a sealing surface 62b. The seals 60, 62 function together to form a closed position as shown in FIG. 3b. More specifically, the sealing surfaces 60a, 62b abut each other. The seals 60, 62 may be made of material such as silicon (e.g., medical-grade silicon), rubber, plastomers, elastomers, or other flexible polymeric materials. The seals 60, 62 need a certain degree of memory. It is contemplated that the spring sections of the seals 60, 62 may also be made of material such as metal.

Figure 4:
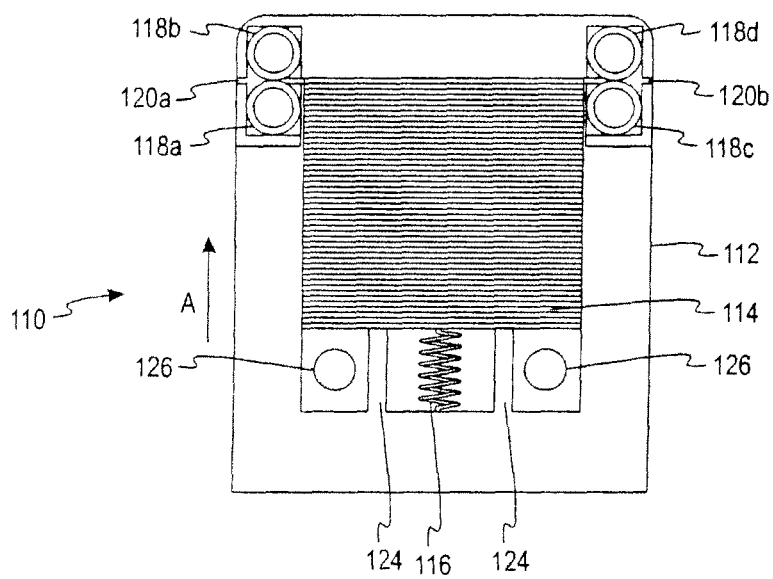
FIG. 4 is a front view of a cartridge according to yet another embodiment of the present invention.

Referring to FIG. 4, a disposable cartridge 110 comprises a housing 112, a plurality of test sensors 114, a mechanical mechanism 116, and a plurality of moveable seals 118. The housing 112 forms at least one opening 120 therethrough. The disposable cartridge 110 also includes prongs or extensions 124 and desiccant material 126.

The plurality of moveable seals 118 includes a first polymeric-hollow tube 118a, a second polymeric-hollow tube 118b, a third polymeric-hollow tube 118c, and a fourth polymeric-hollow tube 118d. The first tube 118a and second tube 118b function together to form a closed position as shown in FIG. 4. The first and second tubes 118a,b are made of flexible material that deforms when a test sensor is inserted therebetween. The first and second tubes 118a,b may be made of material such as silicon (e.g., medical-grade silicon), rubber, plastomers, elastomers, or other flexible polymeric materials. The first and second tubes 118a,b need a certain degree of memory. The third and fourth tubes 118c,d function in a similar manner in that they are made of flexible material that deforms when a bar of the sensor-dispensing instrument is extended therebetween, which will be discussed below in further detail. The third and fourth tubes 118c,d may be made of the same materials as the first and second tubes 118a,b.

The plurality of test sensors 114, mechanical mechanism 116, opening 120, prong or extensions 124 and the desiccant 126 function in a similar manner as described above with respect to test sensors 14, mechanical mechanism 16, opening 20, prong or extensions 24, and the desiccant 26.

Figure 5:
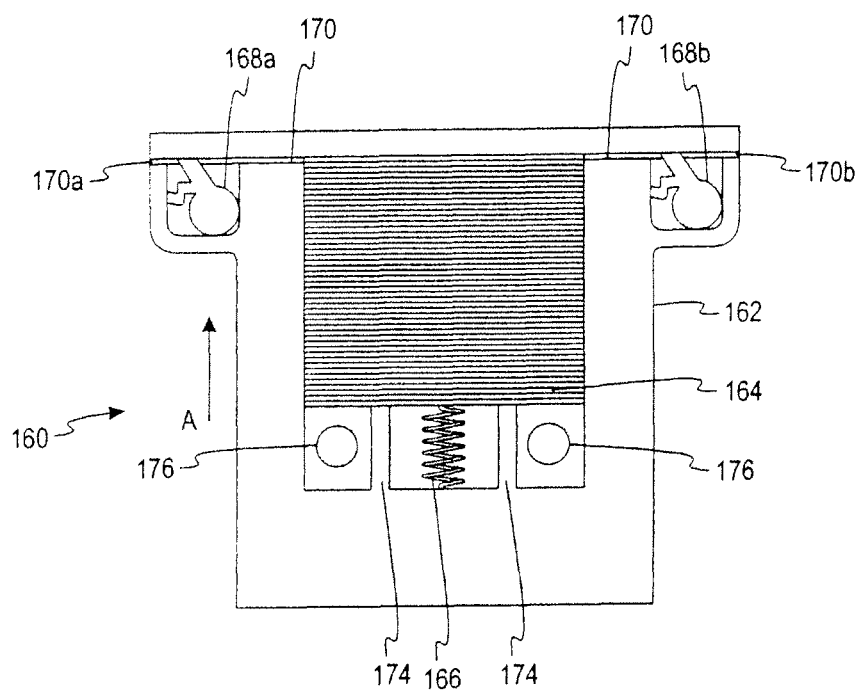
FIG. 5 is a front view of a cartridge according to a further embodiment of the present invention.

Referring to FIG. 5, a disposable cartridge 160 is shown according to another embodiment. The disposable cartridge 160 comprises a housing 162, a plurality of test sensors 164, a mechanical mechanism 166, and a plurality of moveable seals 168a,b. The housing 162 forms at least one opening 170 therethrough. The disposable cartridge 160 also includes prongs or extensions 174 and desiccant material 176.

The moveable seals 168a,b are pivotable seals, which are shown in a closed position in FIG. 5. In the closed position, the pivotable seals 168a,b exert an upward force. When a test sensor is pushed through the opening 170, the pivotable seal 168a pivots downwardly and away from the opening as viewed in FIG. 5 to an open position. The test sensor 164 is allowed to continue thorough to the opening end 170a. The pivotable seals 168a,b may be made of polymeric materials such as silicon (e.g., medical-grade silicon), rubber, plastomers, elastomers, or other flexible polymeric materials. The pivotable seals 168a,b need a certain degree of memory. The pivotable seal 168b is adapted to pivot when a bar of the sensor-dispensing instrument is extended therebetween, which will be discussed below in further detail.

The plurality of test sensors 164, mechanical mechanism 166, opening 170, prong or extensions 174 and the desiccant 176 function in a similar manner as described above with respect to test sensors 14, mechanical mechanism 16, opening 20, prong or extensions 24, and the desiccant 26.

Figure 6:
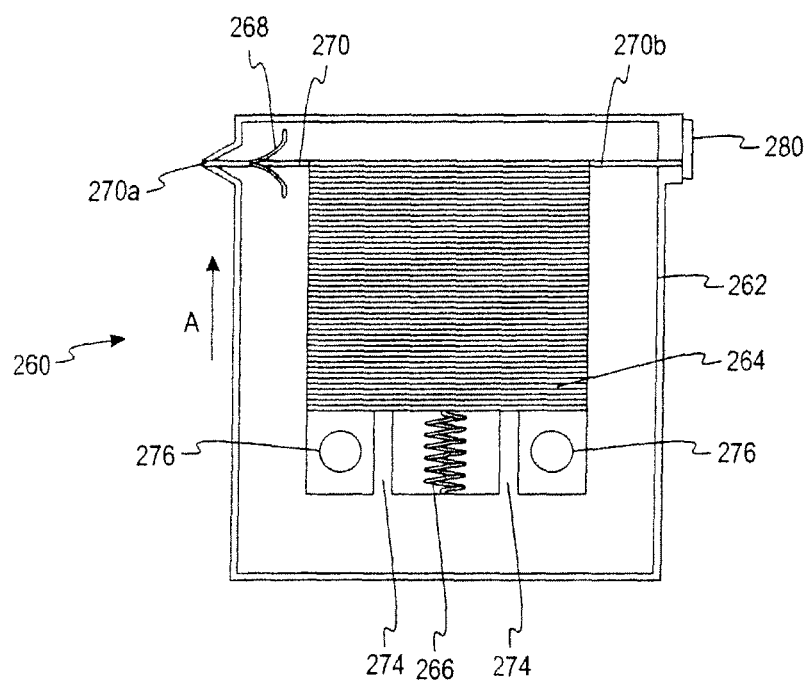
FIG. 6 is a front view of a cartridge according to a further embodiment of the present invention.

It is also contemplated that the disposable cartridge may be only sealed with one moveable seal. One example of such an embodiment is shown in FIG. 6. Referring to FIG. 6, a disposable cartridge 260 is shown according to another embodiment. The disposable cartridge 260 comprises a housing 262, a plurality of test sensors 264, a mechanical mechanism 266, and one moveable seal 268. The housing 262 forms at least one opening 270 therethrough. The disposable cartridge 260 also includes prongs or extensions 274 and desiccant material 276.

The moveable seal 268 is shown in a closed position in FIG. 6 and functions in the same manner as described above with respect to moveable seal 18a. The moveable seal 268 may be made of the same materials as discussed above with respect to moveable seal 18a. The disposable cartridge 260 may include a covering 280. The covering 280 may be removed from the disposable cartridge 260 before the disposable cartridge 260 is placed into a sensor-dispensing instrument. In this embodiment, after removal of the covering 280, the cartridge 260 is not substantially moisture-proof and substantially air-tight until placed in a sensor-dispensing instrument. As will be discussed below, a flat bar will form a fitted or snug seal in the opening 270b after being placed in the sensor-dispensing instrument.

Alternatively, the covering 280 may remain with the disposable cartridge after the disposable cartridge is placed into a sensor-dispensing instrument. In this embodiment, the opening end 270b remains sealed during placement into the sensor-dispensing instrument. In this embodiment, a flat bar will puncture or rupture the covering 280 as will be discussed in more detail below. After being punctured or ruptured, a flat bar will form a fitted or snug seal in the opening 270b after being placed in the sensor-dispensing instrument. The covering 280 may be made of materials such as aluminum foil or polymeric material.

The plurality of test sensors 264, mechanical mechanism 266, opening 270, prong or extensions 274 and the desiccant 276 function in a similar manner as described above with respect to test sensors 14, mechanical mechanism 16, opening 20, prong or extensions 24, and the desiccant 26.

It is contemplated that the disposable container 260 may include a different seal than depicted in FIG. 6. For example, other seals discussed above, may be used such as moveable seals 50, 118, 168, and 218.

Figure 7A:
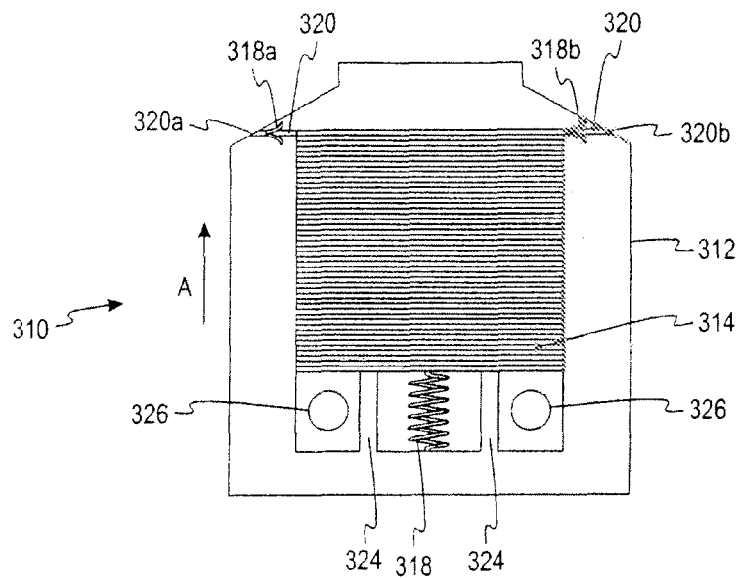
FIG. 7a is a front view of a cartridge according to another embodiment of the present invention.
Figure 7B:
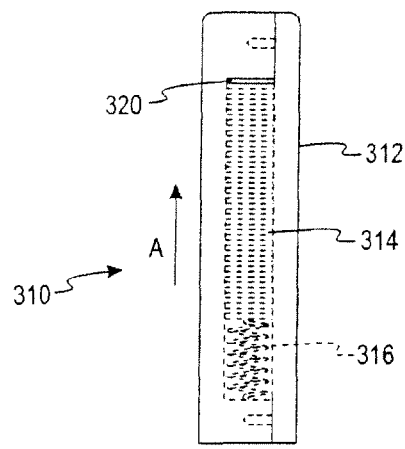

It is also contemplated that other shaped disposable cartridge may be used. For example, referring to FIGS. 7 and 8, a disposable cartridge 310 and a disposable cartridge 360 are depicted. Referring initially to FIG. 7a,b, the disposable cartridge 310 comprises a housing 312, a plurality of test sensors 314, a mechanical mechanism 316, and a plurality of moveable seals 318. The housing 312 forms at least one opening 320 therethrough in which one of the plurality of test sensors 314 eventually exits the cartridge 310 via an opening end 320a. The disposable cartridge 310 and its individual components function similarly as discussed above with respect to the disposable cartridge 10 and its individual components.

The disposable cartridges are advantageous in many aspects. The disposable cartridges are desirably simple to seal, cost-effective and are easy to manufacture in that the process may be performed using a top-down assembly.

Figure 8A:
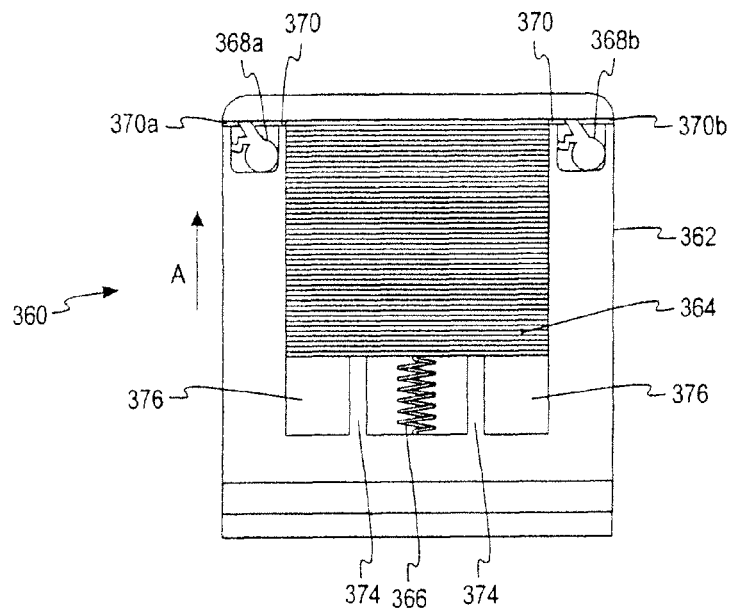
FIG. 8a is a front view of a cartridge according to a further embodiment of the present invention.
Figure 8B:
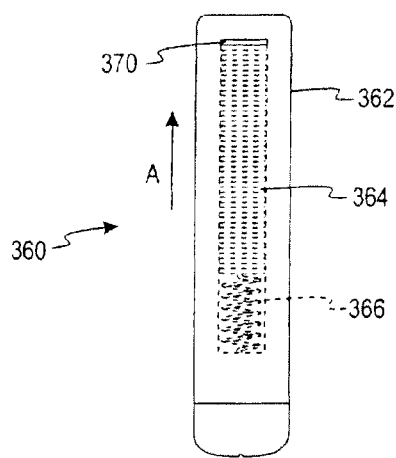

Referring next to FIG. 8, the disposable cartridge 360 is depicted. The disposable cartridge 360 comprises a housing 362, a plurality of test sensors 364, a mechanical mechanism 366, and a plurality of moveable seals 368a,b. The housing 362 forms at least one opening 370 therethrough in which one of the plurality of test sensors 364 eventually exits the cartridge 360 via an opening end 370a. The disposable cartridge 360 also includes an opening end 370b, prongs 374 and desiccant 376. The disposable cartridge 360 and its individual components function similarly as discussed above with respect to the disposable cartridge 10 and its individual components.

Sensor-Dispensing Instrument

Referring to FIGS. 9-14, a sensor-dispensing instrument 400 is depicted according to one embodiment. The sensor-dispensing instrument is used to determine concentrations of analytes. Analytes that may be measured using the present invention include glucose, lipid profiles (e.g., cholesterol, triglycerides, LDL and HDL), microalbumin, hemoglobin $A_1C$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

Figure 10C:
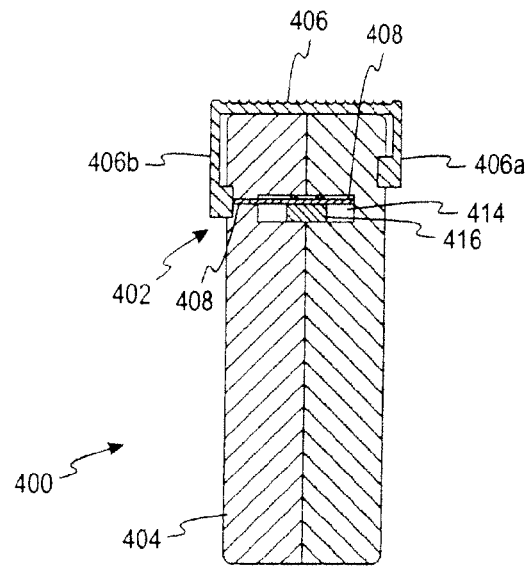
FIG. 10c is a cross-sectional view taken generally along line 10c-10c of FIG. 9.
Figure 11:
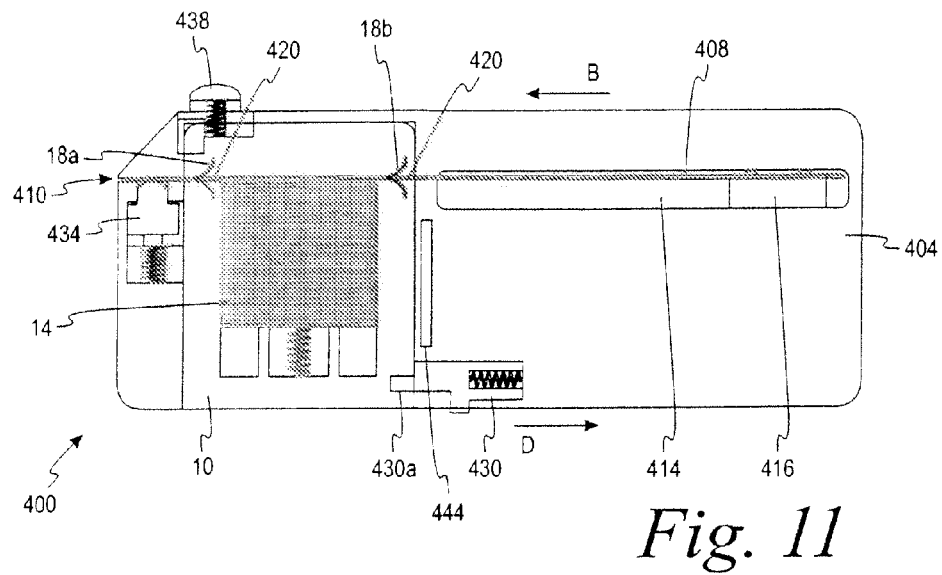
FIG. 11 is an interior view of the sensor-dispensing instrument of FIG. 9 with a flat bar in a first position.
Figure 12:
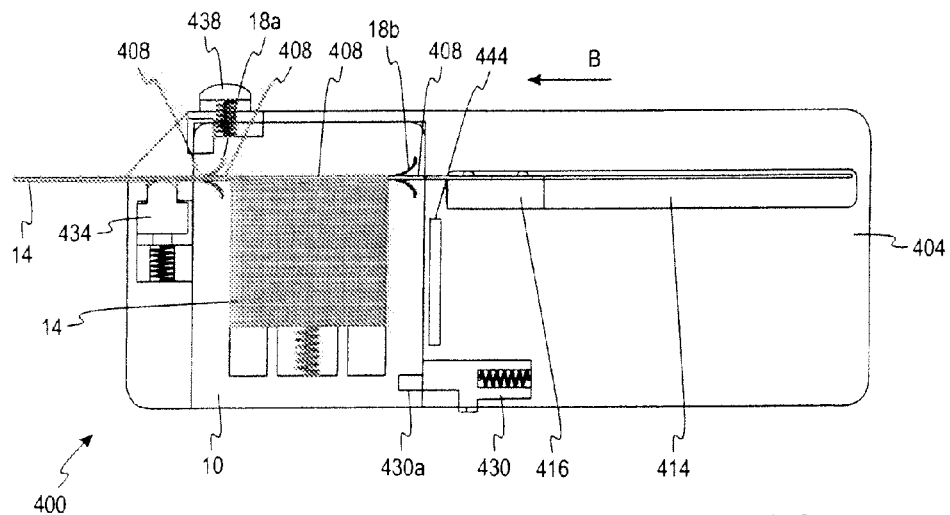
FIG. 12 is an interior view of the sensor-dispensing instrument of FIG. 9 with the flat bar of FIG. 11 in a second position.

The sensor-dispensing instrument 400 comprises a disposable cartridge 10, a pusher assembly 402, and instrument housing 404. As shown in FIG. 10c, the pusher assembly 402 includes a slider 406 and a thin flat bar 408 attached to the slider 406. As shown in FIGS. 11 and 12, the instrument housing 404 is adapted to receive the disposable cartridge 10. It is desirable for the cartridge 10 to be removed from and loaded into the instrument housing 404 of the sensor-dispensing instrument 400 in a simple and easy manner. The instrument housing 404 as shown in FIGS. 11 and 12 loads the disposable cartridge via the bottom. Instead of being a bottom-loading device, the instrument housing may be a side-loading device.

To assist in holding the cartridge 10 in the instrument housing 404, a holding mechanism 430 may be used. The holding mechanism 430 is spring-loaded and includes an extension 430a that corresponds to the notch 22 of the cartridge 10 (see FIG. 1). During the process of loading the cartridge 10, the holding mechanism 430 is pulled back to a first position (in the direction of arrow D of FIG. 11). After the cartridge 10 is positioned in the instrument housing 404, the holding mechanism 430 is released and proceeds to a second position (FIGS. 11 and 12) in which extension 430a engages the notch 22.

It is contemplated that other disposable cartridges may be used, such as those previously described above. Depending on the selected cartridge, the interior of the instrument housing may be redesigned to correspond to the selected disposable cartridge. The instrument housing 404 also forms a dispensing outlet 410, which is sized to dispense the test sensors 14 one at a time.

Figure 9:
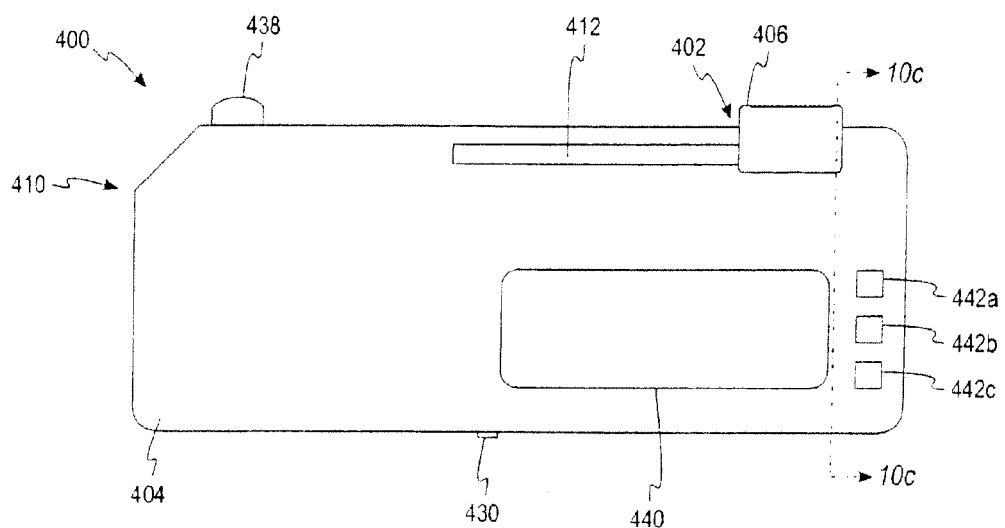
FIG. 9 is a front view of a sensor-dispensing instrument according to one embodiment of the present invention.
Figure 10A:
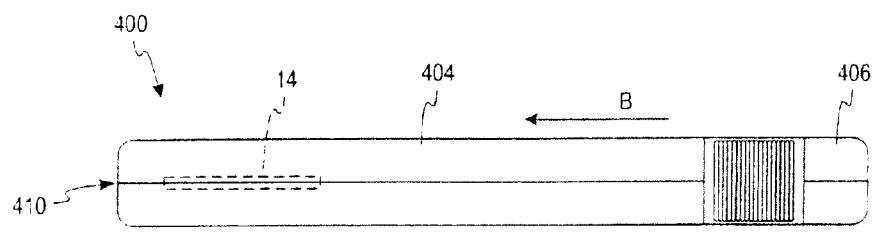
FIG. 10a is a top view of the sensor-dispensing instrument of FIG. 9 with a slider in the first position.

Referring to FIGS. 9 and 10a, the slider 406 is shown in a first position. By continuing to manually move the slider 406 in FIGS. 9 and 10a in the direction of arrow B, the slider 406 is moved to a second position (see FIG. 10b). The slider 406 in FIG. 10b is located closer to the dispensing outlet 410 than the slider of FIG. 10a.

Figure 10B:
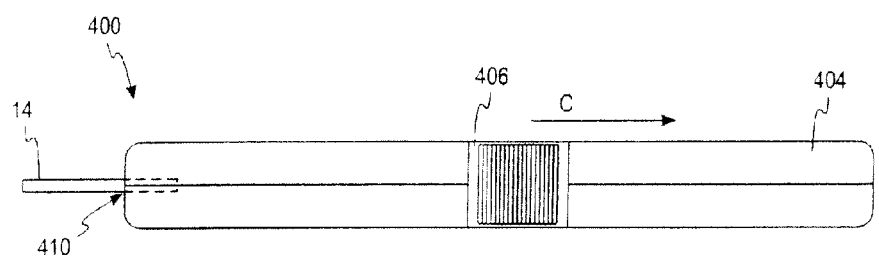
FIG. 10b is a top view of the sensor-dispensing instrument of FIG. 9 with a slider in the second position.

The pusher assembly 402 is adapted to move one of the plurality of test sensors 14 from the disposable cartridge 10 and at least partially through the dispensing outlet 410, such as shown in FIG. 10b. When the slider 406 is in the first position (FIGS. 9 and 10a), the flat bar 408 (which is also in its first position in FIG. 11) does not contact any of the plurality of test sensors 14. As the slider 406 is moved in the direction of arrow B (see FIG. 10a), the flat bar 408 (see FIG. 11) is also moved in the direction of arrow B.

Figure 13:
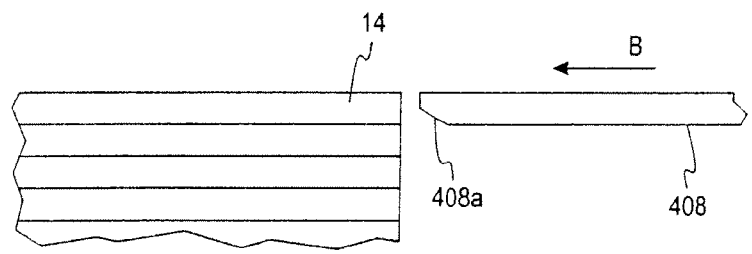
FIG. 13 is an enlarged view of the flat bar just before contacting one of the test sensors according to one embodiment.

Referring to FIG. 13, an enlarged view is shown of the flat bar 408 just before contacting one of the stacked test sensors 14. In this embodiment, the flat bar includes a tapered end 408a. It is desirable to have a tapered end 408a of the flat bar 408 to assist in pushing one of the test sensors from the cartridge, while at the same time preventing the next one of the stacked test sensors from being removed at the same time. It is contemplated that the tapered end may be of different angles than depicted in FIG. 13.

Referring back to FIGS. 9 and 10c, the exterior of the housing 404 forms two external channels. To facilitate easy movement of the slider, the slider 406 of FIG. 9 is shown to move along an external channel 412 and another external channel on an opposing side (see FIG. 10c). More specifically, as shown in FIG. 10c, a depending leg 406a of the slider 406 extends into the channel 412, while a second depending leg 406b extends into the opposing external channel. To enable easier gripping by the user, the slider 406 may form ridges or serrations on a top surface thereof such as show in FIGS. 9 and 10c.

Figure 15:
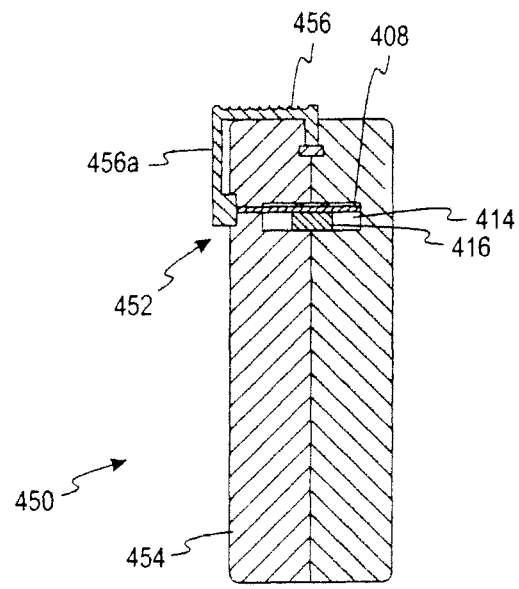
FIG. 15 is a cross-sectional view of a slider according to another embodiment.

It is contemplated that other sliders may be used in the sensor-dispensing instrument. For example, in FIG. 15, a sensor-dispensing instrument 450 is shown that includes a pusher assembly 452, instrument housing 454, and a slider 456. The slider 456 has only one depending leg 456a that engages into a side channel. In this embodiment, the instrument housing 454 forms exactly one exterior side channel for guiding the slider 456 during movement between positions.

Figure 16:
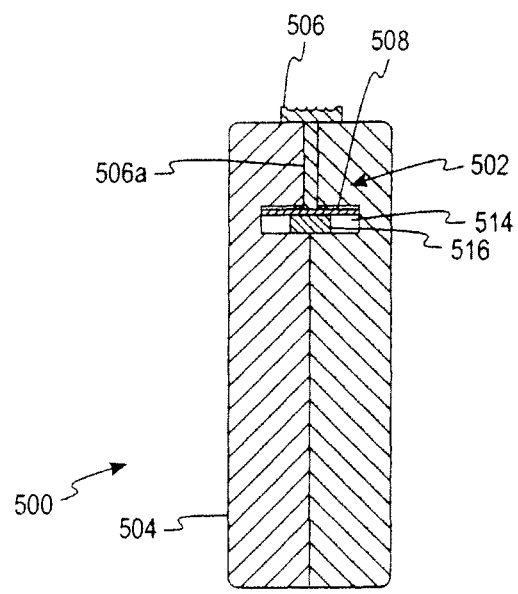
FIG. 16 is a cross-sectional view of a slider according to a further embodiment.

Another example is shown in FIG. 16 with a sensor-dispensing instrument 500 that includes a pusher assembly 502, instrument housing 504, and a slider 506. The pusher assembly 502 of FIG. 16 includes the slider 506 and a flat bar 508 in which the slider 506 is attached to the flat bar 508 via extension 506a. In this embodiment, the instrument housing 504 does not form an exterior side channel for guiding the slider during movement between the first and second positions.

Referring back to FIG. 10c, the flat bar 408 is located in an internal channel 414 that assists in facilitating the movement of the flat bar 408 from a first position (FIG. 11) and a second position (FIG. 12). The pusher assembly 402 also includes a guiding block 416 to further ensure that the flat bar 408 is moving in a proper plane. The guiding black 416 moves along a lower surface of the internal channel 414. Similarly, the slider 506 of FIG. 16 also includes an internal channel 514 and a guiding block 516 to assist in moving and positioning the flat bar 508.

According to one process, the flat bar 408 of FIGS. 11 and 12 extends through an opening 420 and then extends through the moveable seal 18b and subsequently contacts one of the plurality of test sensors 14 (see FIG. 12). The opening 420 properly aligns the flat bar 408 with respect to the moveable seals 18a,b, as well as one of the plurality of test sensors 14. As the slider 406 is continued to be moved in the direction of arrow B in FIG. 10a, the flat bar 408 contacts and pushes one of the plurality of test sensors 14 through seal 18a. As the slider 406 is moved to the second position (see FIG. 10b), the flat bar 408 of FIG. 12 continues to push one of the plurality of test sensors 14 until the sensor has at least partially passed through the dispensing outlet 410.

If electrochemical sensors are used in the sensor-dispensing instrument 400, then one of the test sensors 14 will be positioned appropriately by the flat bar 408 to the electrical contact 434. In other words, the flat bar 408 will push the test sensor to a position that will properly align the test sensor 14 with the electrical contact 434. It is contemplated that the electrical contact 434 includes a plurality of contacts that is positioned to correspond to the test sensor. The front end of the sensor 14 then receives, for example, a drop of blood to be tested, whereby the blood is analyzed by the electrical contact 434. The results of the analysis are then displayed on a liquid crystal display 440 of FIG. 9 (which will be discussed in more detail below) of the sensor-dispensing instrument 400. It is contemplated that other type of sensors may be used such as optical sensors.

The testing end of the sensor is adapted to be placed into contact with the fluid sample (e.g., a whole blood sample) to be tested. The whole blood sample may be generated by a lancing device such as a lancet. The whole blood sample may be obtained by a lancet that may be separate from the sensor-dispensing instrument or may be integrated within the sensor-dispensing instrument. The lancing device may obtain blood by, e.g., pricking a person's finger.

According to one process, the whole blood sample may be prepared by testing by (a) advancing one of the test sensors in position to receive a whole blood sample; (b) generating a whole blood sample; and (c) bringing the test sensor and the whole blood sample into contact wherein the blood is generally drawn into the sensor by capillary action.

The sensors are typically provided with a capillary channel that extends from the front or testing end of the sensors to biosensing or reagent material disposed in the sensor. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that an electrical signal indicative of the blood glucose level in the blood being tested is supplied and subsequently transmitted to an electrical assembly.

After the testing has been completed, the test sensor may be removed by several methods from the sensor-dispensing instrument 400. In one embodiment, the sensor-dispensing instrument may include a eject mechanism 438 that ejects the used test sensor from the sensor-dispensing instrument. In such an embodiment, the test sensors is released forcefully. In another embodiment, the test sensors may be ejected by releasing a grip of the test sensors, resulting in the test sensor being discarded by gravity from the sensor-dispensing instrument. In a further embodiment, the test sensor may also be removed manually from the sensor-dispensing instrument.

As shown in FIG. 12, the flat bar 408 may extend through seal 18a when being moved to the second position. It is contemplated that the flat bar 408 may only extend through only seal 18b when contacting and pushing one of the test sensors. In some embodiments, such as FIG. 6, a flat bar may not extend through any of the moveable seals during the process of pushing the test sensors to and at least partially through the dispensing outlet.

Referring back to FIG. 10b, the slider 406 is moved in the direction of arrow C from its second position to the first position of FIG. 10a. Simultaneously, the flat bar 408 is also moved from it second position to the first position, resulting in the flat bar 408 passing through seals 18a,b. While the slider 406 and the flat bar 408 are in the first position, the cartridge 10 is substantially moisture-proof and air-tight. It is contemplated that the sensor-dispensing instrument may activate the slider mechanism automatically such as in response to pressing a button.

Figure 14:
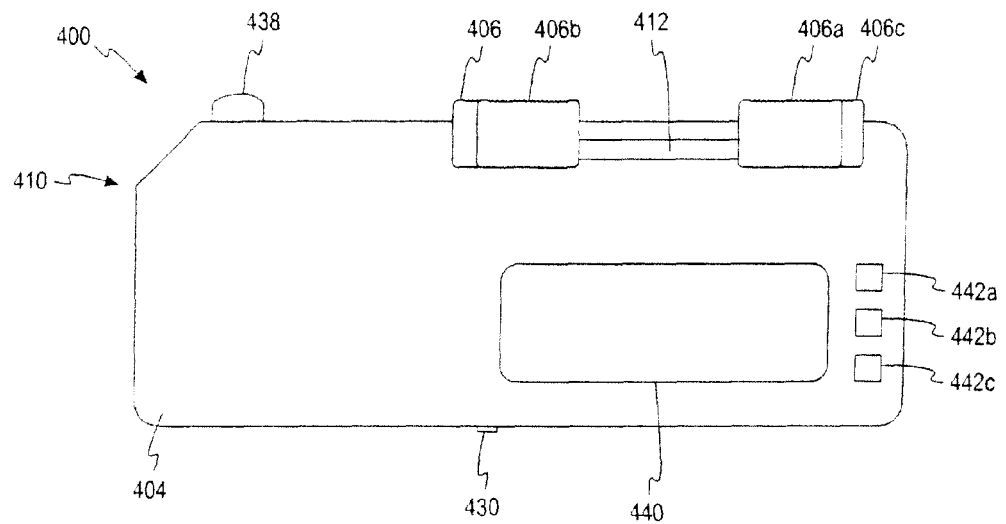
FIG. 14 depicts a front view of a sensor-dispensing instrument with various potential positions of the slider.

FIG. 14 depicts various positions of the slider 406 that may used in various embodiments of a sensor-dispensing instrument. A first position 406a is depicted that is the same position as previously described above with respect to FIGS. 9 and 10a. A second position 406b is depicted that is the same position as previously described above with respect to FIG. 10b. The slider may also be moved to other positions for various functions. For example, in FIG. 14, a slider may be able to proceed to a third position 406c. For improved clarity, only a portion of slider in the third position 406c is shown even though the sliders in each position of FIG. 14 are the same size. The third position 406c of the slider may be used with cartridge 260 of FIG. 6 when the cartridge 260 is being loaded into the sensor-dispensing machine. Thus, when the slider is returned to the first position 406a, the flat bar 408 enters the opening end 270b of the disposable cartridge 260 to form a fitted seal. A slider may have a fourth position 406d that is used to eject a test sensor by force. For improved clarity, only a portion of slider in the fourth position 406d is shown even though the sliders in each position are the same size. It is contemplated that the sensor-dispensing instrument may allow the slider to move to more or less than the positions depicted in FIG. 14.

In certain embodiments of the invention, a spring (not shown) may be attached to the slider 406 that would permit the slider to return to the first position 406a from any other position.

The housing 404 and the slider 406 is typically made of a polymeric materials. Non-limiting examples of polymeric materials include polycarbonate, ABS, nylon, polypropylene, or combinations thereof. Additives may be added to the polymeric material that forms the slider. It is contemplated that the slider may be made of other materials such as metallic materials.

The flat bar 408 also may be made of metal or polymeric material. Some non-limited metallic materials include stainless steel and bronze with appropriate plating. Non-limiting examples of polymeric materials include polycarbonate, ABS, nylon, polypropylene, or combinations thereof. Additives may be added to the polymeric material that forms the flat bar.

The sensor-dispensing instrument 400 also includes a bar code reader 444 (see FIGS. 11 and 12) that reads a bar code label on a disposable cartridge. The bar code reader 444 can determine information such as the lot number and calibration numbers. The sensor-dispensing instrument 400 typically includes a microprocessor or the like for processing and/or storing data generated during the blood glucose test procedure. This data may be displayed on the liquid crystal display 440 of FIG. 9 in the sensor-dispensing instrument 400.

The liquid crystal display 440 displays information from the testing procedure and/or in response to signals input by a button set 442 on the sensor-dispensing instrument 400. For example, the button set may be depressed to recall and view the results of prior testing procedures on the liquid crystal display 440.

The button set 442 comprises several individual buttons 442$a,b,c$ that are depressed to operate the electronics of the sensor-dispensing instrument 400. The buttons may also be depressed to recall and have displayed on the liquid crystal display 440 the results of prior testing procedures. The buttons may also be used to set and display date and time information, and to activate reminder alarms that remind the user to conduct, for example, a blood glucose test according to a predetermined schedule. The buttons may also be used to activate certain calibration procedures for the sensor-dispensing instrument 400.

Some of the information that may be displayed when the sensor-dispensing instrument include the following: a battery indication, a numerical display, an indication of the number of sensors remaining, an indication to load a cartridge into the sensor-dispensing instrument, apply blood indication, a temperature indication, or various combinations thereof.

The sensor-dispensing instrument 400 may also contain an opening for a battery-tray assembly. The battery-tray assembly includes a battery-tray in which a battery is disposed. The battery-tray assembly is inserted into the opening in a side of the sensor-dispensing instrument 400. When so inserted, the battery provides power for the electronics within the instrument 400, including the circuitry on the circuit board assembly (not shown) and the liquid crystal display 440.

Alternative Embodiment A

A disposable cartridge adapted to be used with a sensor-dispensing instrument, the disposable cartridge comprising:
 a housing forming at least one opening therethrough;
 a plurality of test sensors being stacked in the housing, the plurality of test sensors being adapted to assist in testing at least one analyte;
 a mechanical mechanism adapted to urge the plurality of test sensors in a first direction, one of the plurality of test sensors being positioned for ejection from the cartridge; and
 a plurality of moveable seals being adapted to be in a closed position that seals the at least one opening so as to provide a substantially moisture-proof and a substantially air-tight cartridge, and one of the plurality of moveable seals being adapted to be in an open position that allows one of the plurality of test sensors to be moved therethrough.

Alternative Embodiment B

The cartridge according to embodiment A wherein the mechanical mechanism is a spring.

Alternative Embodiment C

The cartridge according to embodiment A wherein the housing forms exactly one opening.

Alternative Embodiment D

The cartridge according to embodiment A wherein each of the plurality of moveable seals is a duckbill seal.

Alternative Embodiment E

The cartridge according to embodiment A wherein each of the plurality of moveable seals is a spring seal.

Alternative Embodiment F

The cartridge according to embodiment A wherein each of the plurality of moveable seals is a hollow tube.

Alternative Embodiment G

The cartridge according to embodiment A wherein each of the plurality of moveable seals is a pivotable seal.

Alternative Embodiment H

The cartridge according to embodiment A wherein the analyte is glucose.

Alternative Embodiment I

The cartridge according to embodiment A further including desiccant.

Alternative Embodiment J

The cartridge according to embodiment A wherein the plurality of sensors is electrochemical sensors.

Alternative Embodiment K

The cartridge according to embodiment A wherein the plurality of sensors is optical sensors.

Alternative Embodiment L

The cartridge according to embodiment A wherein the cartridge comprises a main-housing portion and a lid-housing portion.

Alternative Embodiment M

The cartridge according to embodiment L wherein at least one of the main-housing portion and the lid-housing portion includes at least one energy detectors.

Alternative Embodiment N

The cartridge according to embodiment A wherein the cartridge comprises a notch.

Alternative Embodiment O

A disposable cartridge adapted to be used with a sensor-dispensing instrument, the disposable cartridge comprising:
 a housing forming at least one opening therethrough;
 a plurality of test sensors being stacked in the housing, the plurality of test sensors being adapted to assist in testing at least one analyte;
 a mechanical mechanism adapted to urge the plurality of test sensors in a first direction, one of the plurality of test sensors being positioned for ejection from the cartridge; and
 a moveable seal being adapted to be in a closed position that seals the at least one opening so as to provide a substantially moisture-proof and a substantially air-tight cartridge, the moveable seal being adapted to be in an open position that allows one of the plurality of test sensors to be moved therethrough.

Alternative Embodiment P

A sensor-dispensing instrument comprising:
a disposable cartridge comprising a housing forming at least one opening therethrough, a plurality of test sensors being stacked in the housing, the plurality of test sensors adapted to assist in testing at least one analyte, a mechanical mechanism adapted to urge the plurality of test sensors in a first direction, one of the plurality of test sensors being positioned for ejection from the cartridge; at least one moveable seal being adapted to be in a closed position that seals the at least one opening so as to provide a substantially moisture-proof and a substantially air-tight cartridge, the at least one moveable seal being adapted to be in an open position that allows one of the plurality of test sensors to be moved therethrough;
a housing forming a dispensing outlet and being adapted to receive the disposable cartridge; and
a pusher assembly that includes a slider and a thin flat bar coupled to the pusher assembly, the flat bar being adapted to slide from a first position to a second position on movement of the pusher assembly,
wherein during the movement of the flat bar from the first position to the second position, the flat bar contacts one of the plurality of test sensors and pushes it at least partially through at least one of the moveable seals.

Alternative Embodiment Q

The instrument according to embodiment of P wherein the sensor-dispensing instrument is a blood glucose meter.

Alternative Embodiment R

A disposable cartridge adapted to be used with a sensor-dispensing instrument, the disposable cartridge comprising:
a housing forming at least one opening therethrough;
a plurality of test sensors being stacked in the housing, the plurality of test sensors being adapted to assist in testing at least one analyte;
a mechanical mechanism adapted to urge the plurality of test sensors in a first direction such that one of the plurality of test sensors is positioned for ejection from the cartridge, the mechanical mechanism including a torsion spring; and
a plurality of moveable seals being adapted to be in a closed position that seals the at least one opening so as to provide a substantially moisture-proof and a substantially air-tight cartridge, and one of the plurality of moveable seals being adapted to be in an open position that allows one of the plurality of test sensors to be moved therethrough.

Alternative Embodiment S

The cartridge according to embodiment R wherein the mechanical mechanism further includes a movable pressure plate.

Alternative Embodiment T

The cartridge according to embodiment R wherein the housing forms exactly one opening.

Alternative Embodiment U

The cartridge according to embodiment R wherein each of the plurality of moveable seals is a duckbill seal.

Alternative Embodiment V

The cartridge according to embodiment R wherein the analyte is glucose.

Alternative Embodiment W

The cartridge according to embodiment R further including desiccant.

Alternative Embodiment X

The cartridge according to embodiment R wherein the plurality of sensors is electrochemical sensors.

Alternative Embodiment Y

The cartridge according to embodiment R wherein the plurality of sensors is optical sensors.

Alternative Embodiment Z

A disposable cartridge adapted to be used with a sensor-dispensing instrument, the disposable cartridge comprising:
a housing forming at least one opening therethrough;
a plurality of test sensors being stacked in the housing, the plurality of test sensors being adapted to assist in testing at least one analyte;
a mechanical mechanism adapted to urge the plurality of test sensors in a first direction such that one of the plurality of test sensors is positioned for ejection from the cartridge, the mechanical mechanism including a torsion spring; and
a moveable seal being adapted to be in a closed position that seals the at least one opening so as to provide a substantially moisture-proof and a substantially air-tight cartridge, the moveable seal being adapted to be in an open position that allows one of the plurality of test sensors to be moved therethrough.

Alternative Embodiment AA

A sensor-dispensing instrument comprising:
a disposable cartridge comprising a housing forming at least one opening therethrough, a plurality of test sensors being stacked in the housing, the plurality of test sensors adapted to assist in testing at least one analyte, a mechanical mechanism adapted to urge the plurality of test sensors in a first direction such that one of the plurality of test sensors is positioned for ejection from the cartridge, the mechanical mechanism including a torsion spring; at least one moveable seal being adapted to be in a closed position that seals the at least one opening so as to provide a substantially moisture-proof and a substantially air-tight cartridge, the at least one moveable seal being adapted to be in an open position that allows one of the plurality of test sensors to be moved therethrough;
a housing forming a dispensing outlet and being adapted to receive the disposable cartridge; and
a pusher assembly that includes a slider and a thin flat bar coupled to the pusher assembly, the flat bar being adapted to slide from a first position to a second position on movement of the pusher assembly, wherein during the movement of the flat bar from the first position to the second position, the flat bar contacts one of the plurality of test sensors and pushes it at least partially through at least one of the moveable seals.

Alternative Embodiment BB

The instrument according to embodiment of AA wherein the sensor-dispensing instrument is a blood glucose meter.

While the invention has been described with reference to details of the illustrated embodiment, these details are not intended to limit the scope of the invention as defined in the appended claims. For example, the sensor-dispensing instrument 400 can be used for testing fluids other than blood glucose. In fact, the sensor-dispensing instrument 400 can be used in connection with the analysis of any type of chemistry fluid that can be analyzed by means of a reagent material.

What we claim is:

1. A cartridge, comprising:
   a housing forming a first opening therethrough;
   a plurality of test sensors being stacked in the housing;
   a mechanical mechanism configured to urge the plurality of test sensors in a first direction; and
   a moveable seal including a first hollow tube and a second hollow tube, the first and the second hollow tubes being located relative to each other such that the first and the second hollow tubes are biased to form a closed position of the moveable seal, the moveable seal being entirely enclosed within the housing.

2. The cartridge of claim 1, wherein the first hollow tube has a generally circular cross section and wherein the second hollow tube has a generally circular cross section.

3. The cartridge of claim 1, wherein the moveable seal has a cross section with a generally figure eight shape.

4. The cartridge of claim 1, wherein in response to at least one of the plurality of test sensors proceeding towards an exterior of the housing and being inserted between the first hollow tube and the second hollow tube, the first and the second hollow tubes are configured to deform such that the moveable seal moves from the closed position to an open position.

5. The cartridge of claim 4, wherein the first and the second hollow tubes have a certain degree of memory such that the first and the second hollow tubes are configured to return the moveable seal to the closed position in response to the at least one of the plurality of test sensors being removed from the cartridge.

6. The cartridge of claim 1, wherein a sealing surface of the first hollow tube abuts a sealing surface of the second hollow tube in response to the moveable seal being in the closed position.

7. The cartridge of claim 1, wherein the housing further forms a second opening therethrough, and the moveable seal aids in sealing the first opening.

8. The cartridge of claim 7, further comprising a second moveable seal including a third hollow tube and a fourth hollow tube, the third and the fourth hollow tubes being located relative to each other such that the third and the fourth hollow tubes are biased to form a closed position of the second moveable seal.

9. The cartridge of claim 8, wherein the second moveable seal aids in sealing the second opening.

10. The cartridge of claim 1, wherein the first hollow tube and the second hollow tube include a flexible polymeric material.

11. The cartridge of claim 1, wherein the first hollow tube and the second hollow tube include silicon.

12. The cartridge of claim 1, wherein the first hollow tube is separate and distinct from the second hollow tube.

13. A cartridge, comprising:
    a housing having a first opening;
    a plurality of test sensors stacked in the housing;
    a mechanical mechanism engaging and urging the plurality of test sensors in a first direction; and
    a moveable seal including a first hollow tube and a second hollow tube, the first and the second hollow tubes being located relative to each other such that the first and the second hollow tubes are biased to form a closed position of the moveable seal, wherein a portion of the housing adjacent to the first opening (1) aids in maintaining the relationship between the first hollow tube and the second hollow tube and (2) completely surrounds the first hollow tube and the second hollow tube.

14. The cartridge of claim 13, wherein the first hollow tube has a generally circular cross section and wherein the second hollow tube has a generally circular cross section.

15. The cartridge of claim 13, wherein the first hollow tube and the second hollow tube include a flexible polymeric material.

16. The cartridge of claim 13, wherein the first hollow tube and the second hollow tube include silicon.

17. The cartridge of claim 13, wherein the first hollow tube is separate and distinct from the second hollow tube.

* * * * *